(12) United States Patent
Ram-Liebig et al.

(10) Patent No.: US 7,851,217 B2
(45) Date of Patent: Dec. 14, 2010

(54) PROCESS FOR PRODUCING A TISSUE TRANSPLANT CONSTRUCT FOR RECONSTRUCTING A HUMAN OR ANIMAL ORGAN

(75) Inventors: Gouya Ram-Liebig, Dresden (DE); Ursula Ravens, Dresden (DE); Manfred Wirth, Dresden (DE)

(73) Assignee: UroTec GmbH, Dresden (DE)

( * ) Notice: Subject to any disclaimer, the term of this patent is extended or adjusted under 35 U.S.C. 154(b) by 0 days.

(21) Appl. No.: 11/364,486

(22) Filed: Feb. 28, 2006

(65) Prior Publication Data

US 2006/0233767 A1  Oct. 19, 2006

(30) Foreign Application Priority Data

Apr. 13, 2005  (DE) .................. 10 2005 017 000

(51) Int. Cl.
*C12N 5/00* (2006.01)
*C12N 5/077* (2010.01)

(52) U.S. Cl. ............... 435/325; 435/373; 435/377; 435/395; 435/401

(58) Field of Classification Search ................ 435/325, 435/373, 377, 395, 401
See application file for complete search history.

(56) References Cited

U.S. PATENT DOCUMENTS 6,428,802 B1 * 8/2002 Atala .................. 424/423
2003/0017588 A1 * 1/2003 de Bruijn et al. ........... 435/366
2005/0271635 A1 * 12/2005 Kropp et al. .............. 424/93.7

FOREIGN PATENT DOCUMENTS

WO  WO 98/06445  *  2/1998
WO  WO 9806445 A1 *  2/1998

OTHER PUBLICATIONS

Yoo et al, Urology 51: 221-225, 1998.*
The European Commission Health and Consumer Protection Directorate-General report on the Opinion on the State of the Art Concerning Tissue Engineering, pp. 1-16, 2001.*
Moreno-Borchart, EMBO Reports 5(11): 1025-1028, 2004.*
Griffith and Naughton, Science 295: 1009-1014, 2002.*
Atala, Expert Opin. Biol. Ther. 5(7): 879-892, 2005.*
Williams, Materials Today 7(5): 24-29, 2004.*
Shieh and Vacanti, Surgery 173(1): 1-7, 2005.*
Parnigotto et al, Urol. Res. 28:46-51, 2000.*
Coplen et al, In Vitro Cell. Dev. Biol.—Animal 39:157-162, 2003.*
Deng et al, PNAS 98(1):154-159, 2001.*
Zhang et al, J. Urol. 164:928-935, 2000.*
Selkitar et al, Tissue Engineering 9(4):657-666, 2003.*
Dahms et al, British J. of Urol. 82:411-419, 1998.*
Ram-Liebig et al, BJU International 94(6):922-7, 2004.*
Camoretti-Mercado et al, J. Biol. Chem. 275(39):30387-30393, 2000.*
Kropp et al, J. Urol. 162:1779-1784, 1999.*
Faggian et al, Histochem. Cell Biol. 109:25-39, 1998.*

* cited by examiner

*Primary Examiner*—Kevin K. Hill
(74) *Attorney, Agent, or Firm*—Roger D. Emerson; Nathan B. Webb; Emerson Thomson Bennett (57) ABSTRACT

A process for producing a tissue transplant construct for reconstructing a human or animal organ. The process may include the steps of: (a) isolation and two-dimensional cultivation of organ-specific tissue cells; (b) application of the organ-specific tissue cells to a biocompatible, collagen-containing membrane; and, (c) cultivation of the organ-specific tissue cells on the membrane with biochemical and mechanical stimulation of the organ-specific tissue cells. Tissue transplant constructs and methods for using tissue transplant constructs are also taught.

3 Claims, 6 Drawing Sheets

PROCESS FOR PRODUCING A TISSUE TRANSPLANT CONSTRUCT FOR RECONSTRUCTING A HUMAN OR ANIMAL ORGAN

This application claims priority to German Patent Application No. 10 2005 017 000.5, entitled PROCESS FOR PRODUCING A TISSUE TRANSPLANT CONSTRUCT FOR RECONSTRUCTING A HUMAN ANIMAL ORGAN, filed Apr. 13, 2005, which is incorporated herein by reference.

I. BACKGROUND OF THE INVENTION

A. Field of Invention

This invention relates to a process for producing a tissue transplant construct for reconstructing a human or animal organ, to a tissue transplant construct of this type, and to a use of a tissue transplant construct of this type. The invention relates in particular to a tissue transplant construct for reconstructing the urinary bladder.

B. Description of the Related Art

The urinary bladder consists of the mucosal layer and of the muscle tissue layer. Mucosal cells are urothelial cells which form a mutilayer covering of the interior of the urinary bladder and protect it against urine. The muscle tissue, referred to as detrusor, consist of smooth muscle cells and, located between them, interstitial cells, which comprise fibroblasts or fibroblastic cells. Fibroblastic cells consist of two cell populations, with positive and negative expression of c-kit antibody. The muscle cells are responsible for the contraction, i.e., the emptying of the urinary bladder. The interstitial cells are responsible for transmission of the electrical impulses derived from muscle cells, and thus for the functioning of the muscle cells as a unit.

Reconstruction of the urinary bladder may be necessary because of congenital or acquired disorders such as, for example, meningomyelocele, bladder exstrophy and cloacal exstrophy, traumata, malignant tumors, neuropathic dysfunctions, detrusor instability. Reconstruction of the urinary bladder is effected clinically by using segments of intestine. This is associated with multiple complications such as, for example, infection, incontinence, malignant degeneration, diarrhea, electrolyte disturbance, malabsorption and increased morbidity. It has been proposed to carry out the reconstruction, i.e. the replacement of damaged or diseased regions of a urinary bladder, by means of tissue transplant constructs which are intended to serve as a matrix for regrowth of original tissue. In this connection, the cultivation of patients' own urinary bladder cells on the membrane and thus the in vitro generation of viable bladder tissue has been proposed several times [1, 2, 3]. However, this shows a large number of problems.

In addition, tissue transplant constructs comprising a biological, collagen-containing membrane onto which one or more layers of organ-specific urothelial cells are applied are known for the reconstruction of a human urinary bladder. The outer layer of the urothelial cells is a layer of terminally differentiated tissue cells [4].

However, needed for reconstruction of a urinary bladder also with regard to its physiological function are not only urothelial cells as barrier layer against urine, but also smooth muscle cells in order to enable contraction thereof. However, it has not to date been possible to reconstruct urinary bladder tissue with seeded membranes whose contractility corresponds to that of the natural tissue, because complete generation of muscle cells after implantation has not been achieved. One reason for this is presumably that adult smooth muscle cells lose their more differentiated phenotype in vitro [5, 6]. It is moreover unknown whether smooth muscle cells are in fact able to redifferentiate completely after implantation [6]. On the other hand, the intercellular communication between smooth muscle cells may be impaired through the deficiency of interstitial fibroblastic cells in the tissue transplant construct, possibly leading to a voiding dysfunction after implantation of the construct [7, 8].

II. SUMMARY OF THE INVENTION

It is an object of the invention to eliminate the disadvantages of the prior art. It is intended in particular to indicate a process for producing a tissue transplant construct which resembles, in terms of its physiological contractile functionality, the natural tissue to a greater extent than hitherto.

This object is achieved by the features of claims 1, 20, 25 and 26. Expedient developments of the inventions are evident from the features of claims 2 to 19, 21 to 24.

The patent or application file contains at least one photograph executed in color. Copies of this patent or patent application publication with color photograph(s) will be provided by the Office upon request and payment of necessary fee.

III. BRIEF DESCRIPTION OF THE DRAWINGS

The invention is illustrated in detail by means of examples hereinafter with reference to the drawings. These show FIG. 1B: staining of cellular DNA with DAPI, 100× magnification);

FIGS. 2A-2F are immunohistochemical stains of bladder detrusor cell cultures of passage 3 on acellular membranes using antibodies for alpha smooth muscle actin (FIG. 2A: cultivation without urothelial induction and mechanical stimulation; FIG. 2B: cultivation with urothelial induction and reduction in the serum concentration; FIG. 2C: cultivation with urothelial induction and mechanical stimulation with reduction in serum, day 32, FIG. 2D to 2F: penetrating SMC in the membrane on day 21 of culture with retention of their differentiated phenotype (positive reaction with alpha smooth muscle actin antibody);

FIG. 3B: cultivation of the bladder detrusor cells induced with proliferating urothelium-conditioned medium);

FIGS. 5A-5C are hematoxylin and eosin stains of bladder detrusor cells cultivated with urothelial induction and mechanical stimulation on the membrane (FIG. 5A: cell layers on the membrane; FIG. 5B: penetration of the cells within the membrane in various directions; FIG. 5C: completely penetrated membrane on day 32)

IV. DESCRIPTION OF THE PREFERRED EMBODIMENT

The invention provides a process for producing a tissue transplant construct for reconstructing a human or animal organ, comprising the steps (a) isolation and two-dimensional cultivation of organ-specific tissue cells;

(b) application of the organ-specific tissue cells to a biocompatible, collagen-containing membrane; and (c) cultivation of the organ-specific tissue cells on the membrane with biochemical and mechanical stimulation of the organ-specific tissue cells.

According to the invention, the organ-specific tissue cells are isolated and cultivated two-dimensionally before application to the membrane. After growth of the two-dimensionally cultivated tissue cells, the tissue cells obtained in this way are applied to the membrane and cultivated further there with biochemical stimulation and with mechanical stimulation. The biochemical stimulation and the mechanical stimulation are preferably carried out simultaneously. The mechanical stimulation may moreover take place continuously or at intervals.

The invention is based on the surprising realization that mechanical stimulation of the tissue cells cultivated on the membrane leads to transplant constructs whose membrane is densely permeated by tissue cells, and the tissue cells exhibit their natural phenotype. The tissue cells are preferably muscle tissue cells.

The term "organ-specific tissue cells" is intended in this connection to be understood to mean that tissue cells of the same or of an identical organ which is to be reconstructed are applied to the membrane. If, for example, the intention is to reconstruct a urinary bladder, organ-specific tissue cells mean in this connection urothelial cells and/or muscle tissue cells.

Organs are functional units of the body. The preferred example is the urinary bladder.

The terms "membrane" and "matrix" are used synonymously herein unless indicated otherwise. The membrane ought to comprise the components of the extracellular matrix (ECM), especially the growth factors thereof. The membrane is preferably a biological membrane, particularly preferably a biological membrane which is degraded in the body to nontoxic substances and is replaced by an endogenous tissue structure.

A collagen-containing membrane is intended in this connection to be understood to mean a membrane chiefly based on collagen.

For example, the membrane can be selected from the group comprising acellular urinary bladder, acellular urinary bladder submucosa, acellular aorta, acellular dermal matrix, acellular urethra, and acellular small intestinal submucosa.

Reconstruction means the replacement of damaged or diseased regions of a human or animal organ, especially of a urinary bladder.

The tissue cells are preferably muscle tissue cells, more preferably muscle tissue cells of the urinary bladder. The muscle tissue cells are particularly preferably smooth muscle cells and interstitial fibroblastic cells of the muscle tissue layer of the urinary bladder in the natural ratio thereof. Muscle tissue cells of the urinary bladder are also referred to hereinafter as detrusor tissue cells or detrusor cells.

Biochemical stimulation means in this connection urothelial induction and serum induction. A preferred example of the biochemical stimulation is mitogenic stimulation of the urothelium and of the serum.

In a preferred embodiment, the muscle tissue cells are cultivated with mitogenic stimulation after they have been applied to the membrane. The muscle tissue cells which are applied to the membrane are preferably two-dimensionally cultivated muscle tissue cells of passages 2 to 7, more preferably 3 to 6, most preferably of passage 3.

Cultivation of the muscle tissue cells in step (c) should take place with urothelial induction and adapted serum concentration. Urothelial induction can take place by using a medium which has been conditioned by means of urothelium. The medium in this case may be a medium conditioned with proliferating urothelium or a medium conditioned with terminally differentiated urothelium.

"Proliferating urothelium" or "proliferative urothelium" means urothelial cells which have proliferated on an acellular membrane in a culture medium with a constant addition of FCS or autologous serum (for example 5%). The urothelial cells were then incubated in DMEM, and the medium was harvested. This medium is referred to as medium conditioned with proliferating urothelium. This medium can subsequently be supplemented with FCS or autologous serum.

"Autologous serum" means patient's or animal's own serum, or serum, from whose the muscle tissue cells were taken.

"Terminally differentiated urothelium" means urothelial cells which have proliferated on an acellular membrane in a culture medium with a decreasing addition of FCS or autologous serum (for example from 5% to 1%) with fibroblastic induction. The urothelial cells were then incubated in DMEM, and the medium was harvested. This medium is referred to as medium conditioned with terminally differentiated urothelium. This medium can subsequently be supplemented with FCS or autologous serum.

The urothelium may derive from the mucosal layer of the urinary bladder, preferably of the urinary bladder from whose muscular layer the muscle tissue cells were taken. Fibroblasts used to induce the terminally differentiated urothelial cells can be obtained from the submucosal layer of the same urinary bladder.

Cultivation of the muscle tissue cells in step (c) should take place in a medium which has been conditioned by means of urothelium and which additionally comprises fetal bovine serum (FCS) or autologous serum. The medium preferably comprises 5% of FCS or autologous serum. In a preferred embodiment, the concentration of FCS or autologous serum is reduced stepwise to 0% during the cultivation of the muscle tissue cells on the membrane.

Two-dimensional cultivation means cultivation in a plane, for example on the base of a culture flask. Three-dimensional cultivation means cultivation in a three-dimensional space, for example in such a way that the tissue cells cover the membrane surface and additionally permeate the membrane.

The mechanical stimulation in step (c) of the process of the invention can be carried out by stretching the membrane onto which the tissue cells are applied. The membrane may undergo static and/or cyclic stretching. Accordingly, the mechanical stimulation may comprise (c1) stretching of the membrane for a preset period;

(c2) relaxation of the membrane for a preset period; and (c3) n-fold repetition of steps (c1) and (c2), where n is an integer greater than or equal to 1.

If the mechanical stimulation is carried out by stretching the membrane, the membrane is preferably stretched along its long axis.

In a preferred embodiment, the muscle tissue cells and the urothelium are derived from a urinary bladder, particularly preferably from the same urinary bladder.

The invention is particularly suitable for producing a tissue transplant construct for reconstructing the urinary bladder. A process for producing a tissue transplant construct for reconstructing the urinary bladder comprises (a*) isolation and two-dimensional cultivation of muscle tissue cells of the urinary bladder;

(b*) application of the muscle tissue cells to a biocompatible, collagen-containing membrane; and (c*) cultivation of the muscle tissue cells on the membrane with urothelial induction and adapted serum concentration and with mechanical stimulation of the muscle tissue cells.

The muscle tissue cells comprise smooth muscle cells and interstitial fibroblastic cells preferably in their natural ratio.

After the muscle cells of the urinary bladder have been applied to the membrane they are preferably cultivated with mitogenic stimulation. The muscle tissue cells of the urinary bladder which are applied to the membrane are particularly preferably two-dimensionally cultivated muscle tissue cells of passages 2 to 7, more preferably 3 to 6, most preferably passage 3. It must be taken into account in this connection that the growth potential of the cells decreases as the number of two-dimensional passages increases.

The cultivation of the muscle tissue cells of the urinary bladder in step (c*) should be carried out in a medium that is a medium conditioned with urothelium, preferably a medium conditioned with proliferating urothelium. The concentration of serum (FCS or autologous serum) is preferably reduced during the cultivation stepwise, for example in three steps, for example from 5% to 1% to 0%.

The muscle tissue cells employed for producing a transplant construct for reconstructing the urinary bladder are smooth muscle cells and fibroblastic cells, preferably in their natural ratio as found in the muscular layer of a natural healthy urinary bladder. The smooth muscle cells and fibroblastic cells can be obtained from the muscular layer of a urinary bladder by separating the muscular layer of urothelium, lamina propria and serosa. The muscular layer treated in this way is then comminuted and treated with collagenase. The individual cells can be obtained by centrifugation, cultivated two-dimensionally and passaged at confluence.

It is possible by means of the process of the invention for the first time to obtain tissue transplant constructs which have biocompatible membranes permeated by tissue cells with the natural phenotype. Because of the high degree of permeation, the membranes have a three-dimensional network of tissue cells, i.e. in the case of muscle tissue cells of the urinary bladder a three-dimensional network of smooth muscle cells and fibroblastic cells, with latter cells consisting of c-Kit positive and c-Kit negative cells. The presence of interstitial fibroblastic cells promotes intercellular communication of the smooth muscle cells and is therefore important for the physiological functionality, especially the contractility, of the transplant construct after its implantation.

In a preferred embodiment, the process of the invention comprises the isolation of muscle tissue cells from a urinary bladder biopsy; the two-dimensional proliferation of the muscle tissue cells in a culture flask; the application of the proliferated muscle tissue cells of passage 3 (P3 cells) to the surface of a biocompatible membrane; and the cultivation of the P3 cells with (i) urothelial induction using a medium conditioned with proliferating urothelium and (ii) serum induction and (iii) mechanical stimulation.

If the urothelial induction is carried out for 32 days, then the serum induction comprises reducing the serum concentration from 5% (days 1 to 14) to 1% (days 15 to 28) and then further to 0% (days 29 to 32). The mechanical stimulation is maintained throughout the urothelial induction (32 days), with the membrane preferably being cyclically stretched and relaxed.

The membrane surface is preferably up to 40 $cm^2$ in size.

The invention further provides a tissue transplant construct for reconstructing a human or animal organ which comprises (a) a biocompatible, collagen-containing membrane; and (b) organ-specific tissue cells which have been cultivated on the membrane with biochemical and mechanical stimulation.

The tissue transplant construct of the invention is thus a tissue transplant construct capable of contraction.

Such a tissue transplant construct can be obtained by means of the process of the invention. The organ-specific tissue cells are preferably muscle tissue cells of a urinary bladder. The muscle tissue cells of the urinary bladder are smooth muscle cells and interstitial fibroblastic cells, preferably in their natural ratio.

The tissue transplant constructs of the invention can be used to reconstruct a human or animal organ, preferably to reconstruct human or animal urinary bladder.

The advantageous results are based on the following findings: after application of the tissue cells to the membrane, the dynamic process of cell migration to the membrane was the response to the migration signals provided by the matrix of the membrane. There are evidently receptive proteins on the cell surface which communicate these migration signals into the interior of the cell.

Under the mitogenic effects of FCS or autologous serum, cells of passage 3 (called P3 cells) were capable of confluent covering of membrane surfaces of up to 40 $cm^2$ within a few days, whereas covering of the membrane by P7 cells from a similar size biopsy (i.e. cells after seven passages in the culture flask under conventional conditions) was incomplete. These results suggest that the cells increasingly lose their ability to proliferate as the number of passages increases in two-dimensional cultures under conventional conditions in a culture flask.

A major function of SMC is contraction. Through dedifferentiation, urinary bladder SMCs cultivated two-dimensionally under conventional conditions lose their contractility response to various in vivo agonists [5]. On the other hand, the potential ability of cells which have dedifferentiated in vitro to redifferentiate is unknown [6]. Considering that cellular tissue engineering with urinary bladder SMCs is intended for clinical applications, the tissue cells should have their appropriate phenotype for functioning of the transplant when it is implanted in the host. For this reason, the tissue cells were seeded on three-dimensional biomaterials even at passage 3, in order to make it possible for them to maintain at least partly their differentiated phenotypes by proliferating sufficiently early in three dimensions through interaction with the supporting extracellular matrix. Consequently, the physiological environment influenced the behavior of the cells [9, 10, 11]. When tissue cells were in fact cultivated two-dimensionally under conventional conditions for seven passages before they were applied to the membrane, only less than 5% of the tissue cells stained positively with SMA antibodies, whereas about 20% of the P3 cells expressed SMA when they were cultivated under the same conditions.

It is known that in regeneration of the urinary bladder epithelium-stroma interactions regulate SMC proliferation and differentiation [12, 13]. In order to find out how detrusor cells respond to epithelial stimuli on acellular membranes, tissue cells which were cultivated with media which had been conditioned by urothelium (i.e. epithelial cells of the urinary bladder) were characterized. The urothelium used for this purpose was proliferative in one case and terminally differentiated in another. In fact, proliferative urothelium had a stronger proliferative effect on the cell cultures, whereas only a smaller effect was achieved by terminally differentiated urothelium. In any event, the urothelium-conditioned medium with proliferative urothelial cells and stepwise reduced concentration and later the absence of serum [14] increased SMA protein expression, although it was unable to induce SMA protein expression completely (60%).

It is known that mechanical strain induces SMC in various ways, i.e. proliferation, differentiation, formation of extracellular matrix and growth factors [15-19]. It is of interest that some of these effects are characteristic of a more highly differentiated phenotype, whereas others indicate a more synthetic proliferating, i.e. less differentiated, state. The present invention has achieved, through mechanical stimulation, a more extensive growth of tissue with increased expression of SMA. In addition, the tissue cells showed a different motility pattern than under conditions without mechanical stimulation. In the latter case, more persistent cells usually moved in two directions over the membrane surface. With mechanical stretching and relaxation, less persistent cells penetrated in a plurality of directions into the interior of the membrane by overcoming the matrix resistance through the three-dimensional structure thereof being degraded. The use of the mechanical stimulation in urothelium-conditioned cultures made it possible for the SMCs to show their differentiated phenotypes when the mitogenic effect of serum was reduced and subsequently eliminated. In this case, about 80% of the tissue cells were SMA-positive. SMA is a marker of the differentiated phenotype of SMC.

The insoluble signals of the three-dimensional extracellular matrix which interact with the soluble factors of the urothelium conditioned medium, and mechanical forces in the stepwise-adapted serum concentration promoted the migration, division and differentiation of SMC. Induction of SMC differentiation as response to the urothelium-conditioned medium is characteristic of an endogenous regulatory mechanism. In addition, the results of the present invention show that SMC registers the mechanical strain which additionally induces the cell differentiation. These results show that the effects of the mechanical environment indicate ways other than growth factor/receptor binding. It is possible on the basis of these findings to develop effective cellular strategies for a more proliferative or differentiated activity of tissue cells in order to improve tissue development.

The detrusor is well known to have an extensive network of interstitial fibroblastic cells. In the examples described below, about 20% of the isolated detrusor cell population stained positively for vimentin but negatively for SMA, confirming results of others [8]. C-Kit like immunoreactivity of the latter cells showed 15-20% of them, expressing positively this antibody. The fibroblasts moreover showed only weak immunoreactivity in response to biochemical and mechanical stimuli which induced differentiation of SMC. Since it is assumed that the dissemination of activating impulses in the bladder is mediated by interstitial fibroblastic cells, the presence of these cells in our model system may improve the features of the functionality of the transplant after implantation.

EXAMPLES

The following examples illustrate the process of the invention for producing urinary bladder tissue transplant constructs.

Unless indicated specifically, the abbreviations used have the following meaning:
BCECF 2',7'-Bis-(2-carboxyethyl)-5/6-carboxyfluorescein
DAPI 4',6-Diamidino-2-phenylindole
DMEM Dulbecco's modified Eagle's medium,
ECM Extracellular matrix,
FB Fibroblast
FCS Fetal bovine serum
PI Propidium iodide
SIS Small intestinal submucosa
SMA Alpha smooth muscle actin
SMC Smooth muscle cells Materials and Methods Production of acellular tissue membranes: Acellular tissue membranes (also referred to herein as acellular membranes) were produced from samples of porcine or human urinary bladder, urinary bladder submucosa, aorta, urethra, small intestine and skin. They were obtained in acellular form in Triton X 1% (Sigma-Aldrich, Taufkirchen, Germany) in the presence of 0.1% sodium azide, stirring in a water bath at 37° C. for 24 to 48 h. The extraction of all cellular elements was confirmed histologically. In addition, lyophilized small intestinal submucosa (SIS) was provided by Cook Biotech (Mönchengladbach, Germany).

Cell isolation, culture and characterization: The muscular layer of samples of porcine (n=8) and human (n=4) urinary bladder (0.5×0.5 cm) was dissected from the urinary tract epithelium, lamina propria and serosa, comminuted and treated with collagenase B 0.5% for 2 h (Worthington Biochemical, Lakewood, N.J., USA). Individual cells were collected by centrifugation, and the pellets were transferred into culture flasks comprising DMEM (Invitrogen, Karlsruhe, Germany), supplemented with 5% serum. The cells were cultivated to confluence. P3 and P7 cells were cultivated on the surfaces of acellular membranes (up to 40 cm$^2$). The cultivated cells were analyzed histologically and immunohistochemically using hematoxylin and eosin staining (H & E), SMA antibodies and vimentin and c-Kit antibodies (Dako, Glastrup, Denmark). The apoptosis index was determined with 4',6-diamidino-2-phenylindole (DAPI), and the vitality of the cells with 2',7'-biscarboxyethyl-5 and 6-carboxyfluorescein (BCECF) and propidium iodide (PI) (both MoBiTec, Göttingen, Germany).

Urothelium-conditioned media. In order to produce urothelium-conditioned media, urothelial cells (obtained from the mucosal layer of samples of the same urinary bladder) were cultivated on the surface of acellular membranes. As in [4], urothelial cells were maintained in two different groups, either in a proliferative phenotype in the presence of 5% serum or terminally differentiated by reducing the serum concentration to 1% with fibroblastic induction (from the lamina propria of the same urinary bladder). Urothelial cells were then incubated in DMEM for 24 h, and the conditioned media were harvested. Detrusor cells cultivated on scaffolds were in each case fed with medium conditioned with proliferating or with terminally differentiated urothelium, with the serum concentrations explained below.

Serum-conditioned media. Serum was supplemented to urothelium-conditioned media, i.e. medium conditioned either with proliferative or with terminally differentiated urothelium, at a constant concentration of 5% from day 1 to day 32. Alternatively, serum was reduced in three steps: 5% from day 1 to 14, 1% to day 28 and subsequently serum-free condition for 4 days. The cells in the control groups were cultivated with media which comprised the same serum concentrations but lacked the urothelial conditioning. The culture media were changed every three days, except in serum-free conditions when they were changed each day, in order to ensure the availability of sufficient nutrients for the cells.

Figure 1:
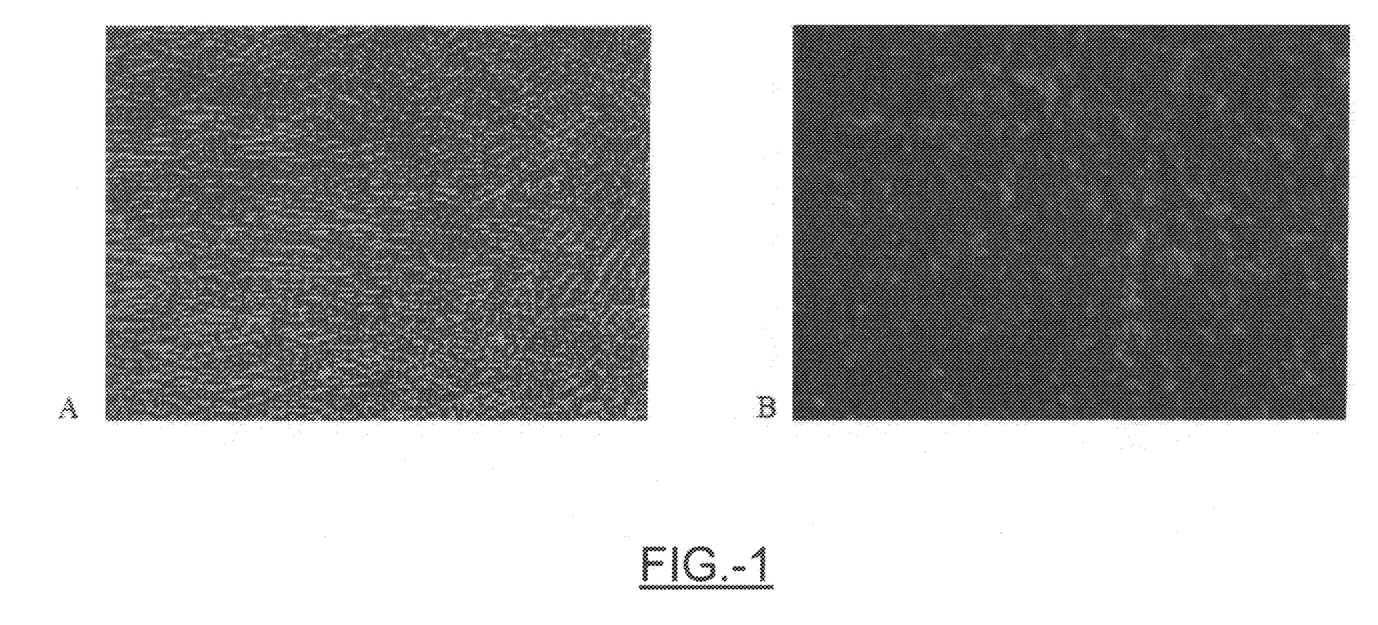
FIGS. 1A-1B are photographs to characterize bladder detrusor cells on an acellular tissue membrane (FIG. 1A: staining with BCECF, 40× magnification.

Mechanical stimulation. A special bioreactor was used to detect the effects of mechanical stimulation on the membrane-cell composites. Membranes seeded with cells were subjected to a stretching by 10% of the surface area, generating a passive stretching of the cells. The device consisted of a motor-driven system which made it possible to exert a mechanical stretching simultaneously on four membranes of rectangular shape (FIG. 1). The membrane-cell composites, i.e. the membrane to which the tissue cells had been applied, were placed in sterile chambers in parallel. The media were injected separately through a roller pump into the different chambers at 1 ml/h and collected in a sterile bottle on the opposite side. The cultures were supplied with 95% air and 5% $CO_2$ at 37° C. The membranes were uniformly stretched in the horizontal direction and fastened between two plates on each side. The effects of the mechanical stretching were investigated with continuous stretching and with cyclic stretching and relaxation (20 s of stretching and 10 s of relaxation or 10 s of stretching and 10 s of relaxation).

The mechanical stretching can be carried out by means of a bioreactor. Details of the bioreactor are described in DE 101 51 822.

Results

The detrusor cells freshly isolated from porcine or human urinary bladder displayed a spindle-shaped morphology, and about 80% of the cells stained positively with antibodies against SMA, and about 20% were vimentin-positive cells showing no SMA expression. A subpopulation of SMA-negative cells stained positively with c-Kit antibodies. The fraction of SMA-positive cells reduced as the number of passages under 2D conditions increased and was less than 60% at passage 7, a variability being found between different animals and patients.

No great differences between cell cultures on the matrices from different sources were detectable. Fluorescence microscopic analyses (FIG. 1) showed that the cells adhered to the scaffold and remained viable for up to 32 days (>80%). DAPI staining of cultivated cells on the membranes showed cell nuclei with an apoptosis rate of less than 20%.

FIG. 1 shows photographs to characterize the tissue cells on the membrane. FIG. 1A shows in 40× magnification an assay to determine the viability of the tissue cells on the membrane. The dye used was BCECF (green color). The fluorescent dye BCECF is specifically for living cells and showed a high cell viability of the tissue cells 32 days after application of the tissue cells to the membrane. FIG. 1B shows in 100× magnification stainings of cellular DNA with DAPI. Several dividing cell nuclei are evident on the membrane 14 days after application of the tissue cells.

Histological analyses showed that P3 cells were distributed uniformly on the surface of the membrane five days after application, whereas P7 cells, which were obtained from biopsies of similar size, show only partial and less uniformly distributed growth. The cell populations on the membranes on day 32 were almost 10 times higher with P3 cells than with P7 cells. However, the percentage of cells positively staining for SMA fell substantially to about 20% in cultures with P3 cells and to 5% in cultures with P7 cells when the cells were cultivated on the surface of larger membranes (>10 $cm^2$).

Although removal of serum led to suppression of cell proliferation and migration, it did not effectively induce differentiation of SMC on the membranes (about 30% expression of SMA in P3 cells, 5 to 10% in P7 cells on day 32).

Figure 2:
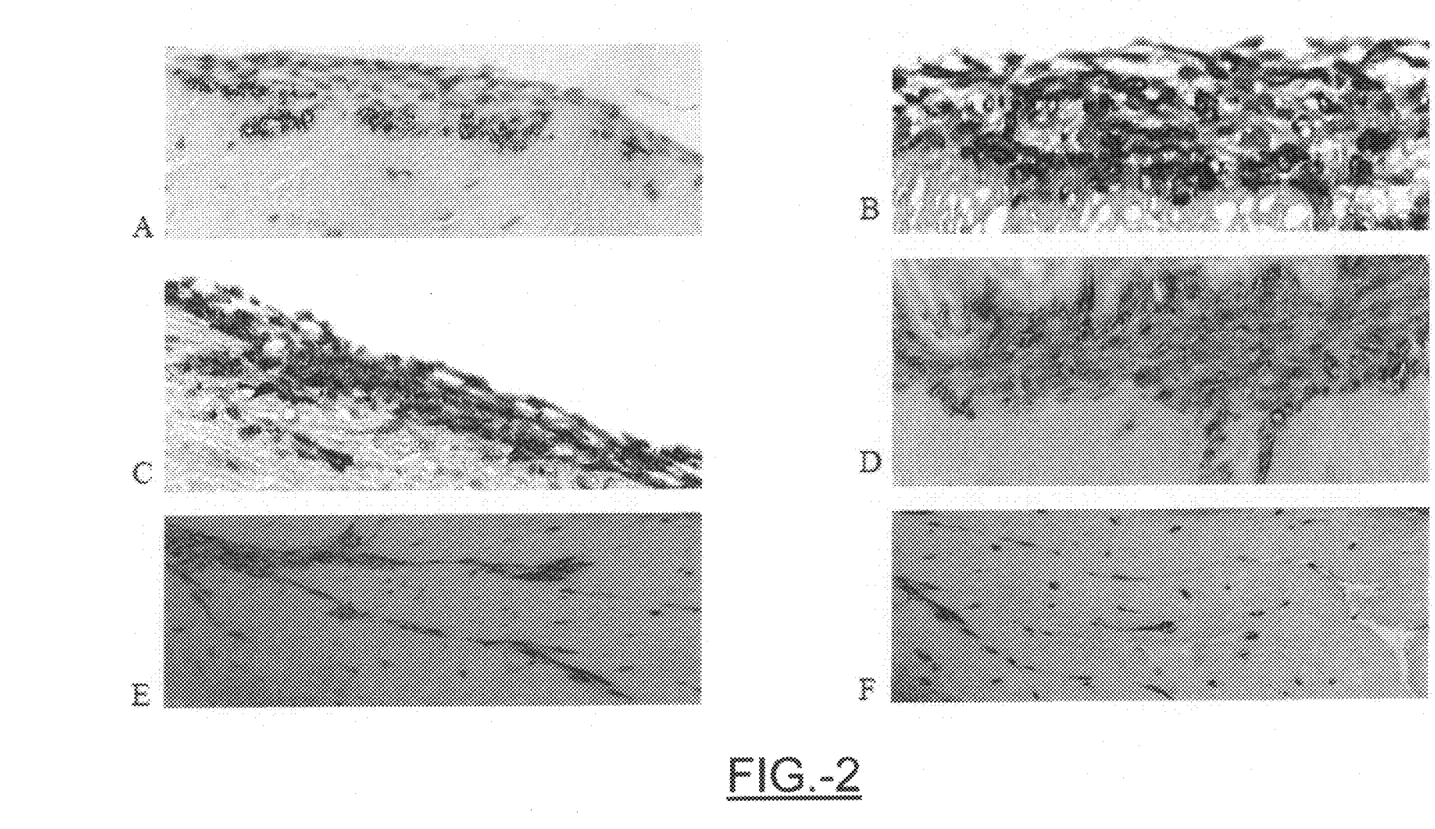

FIGS. 2A to 2F show photographs of immunohistochemical analyses of membrane-cell composites using SMA antibodies, in each case in 20× magnification. Tissue cells of passage 3 were transferred to the membrane. FIG. 2A shows cultivated tissue cells without urothelial induction and without mechanical stimulation. These tissue cells showed about 20% positive staining with SMA antibody (brown color) after 32 days. FIG. 2B shows that about 60% of the tissue cells had a differentiated (mature) phenotype on the membrane surface on day 32 after removal of serum when the tissue cells were cultivated in medium conditioned with proliferative urothelium. FIGS. 2C to 2F show cells cultivated on the membrane surface with urothelial induction and mechanical stimulation. More than 80% of the cells showed positive reactions with SMA antibody on day 32 after removal of serum (FIG. 2C). In serum-reduced medium (1% FCS), tissue cells had reached the interior of the membrane on day 21 with urothelial and mechanical stimulation, and the tissue cells have retained their differentiated phenotype (FIG. 2D to FIG. 2F).

Figure 3:
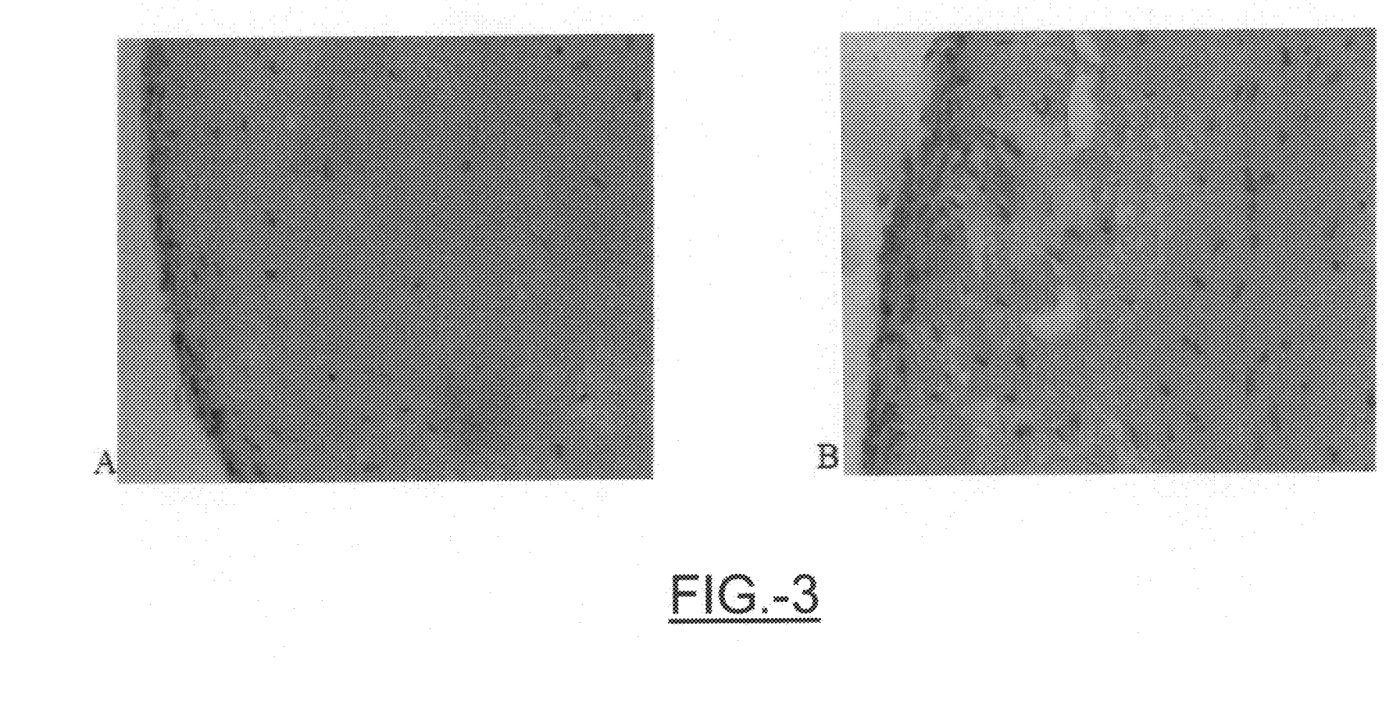
FIGS. 3A-3B are hematoxylin and eosin stains with bladder detrusor cells cultivated with urothelial induction and without mechanical stimulation on day 18 on the membrane (FIG. 3A: cultivation of the bladder detrusor cells induced with terminally differentiated urothelial medium.

Cell proliferation and migration was induced by a medium which had been conditioned with proliferating urothelium. In fact, P3 cells cultivated in this medium formed 3 to 5 layers on the surface of the membrane by day 18, whereas cultures fed with medium conditioned with terminally differentiated urothelium formed only 1 to 2 layers of cells (FIG. 3).

FIGS. 3A and 3B show photographs of H & E staining of cultivated membrane-cell composites on day 18 after application of the P3 tissue cells to the membrane in 20× magnification. In the culture system conditioned with terminally differentiated urothelium without mechanical stimulation, the tissue cells formed 1 to 2 layers and then penetrated into the membrane (FIG. 3A). By comparison with this system, the medium which had been conditioned with proliferating urothelium induces greater proliferation of the P3 tissue cells and penetration of the membrane (FIG. 3B). In fact, 3 to 5 cell layers were identifiable on the surface of the membrane, which is likewise permeated with more cells which have penetrated in the membrane (FIG. 3B).

Figure 4:
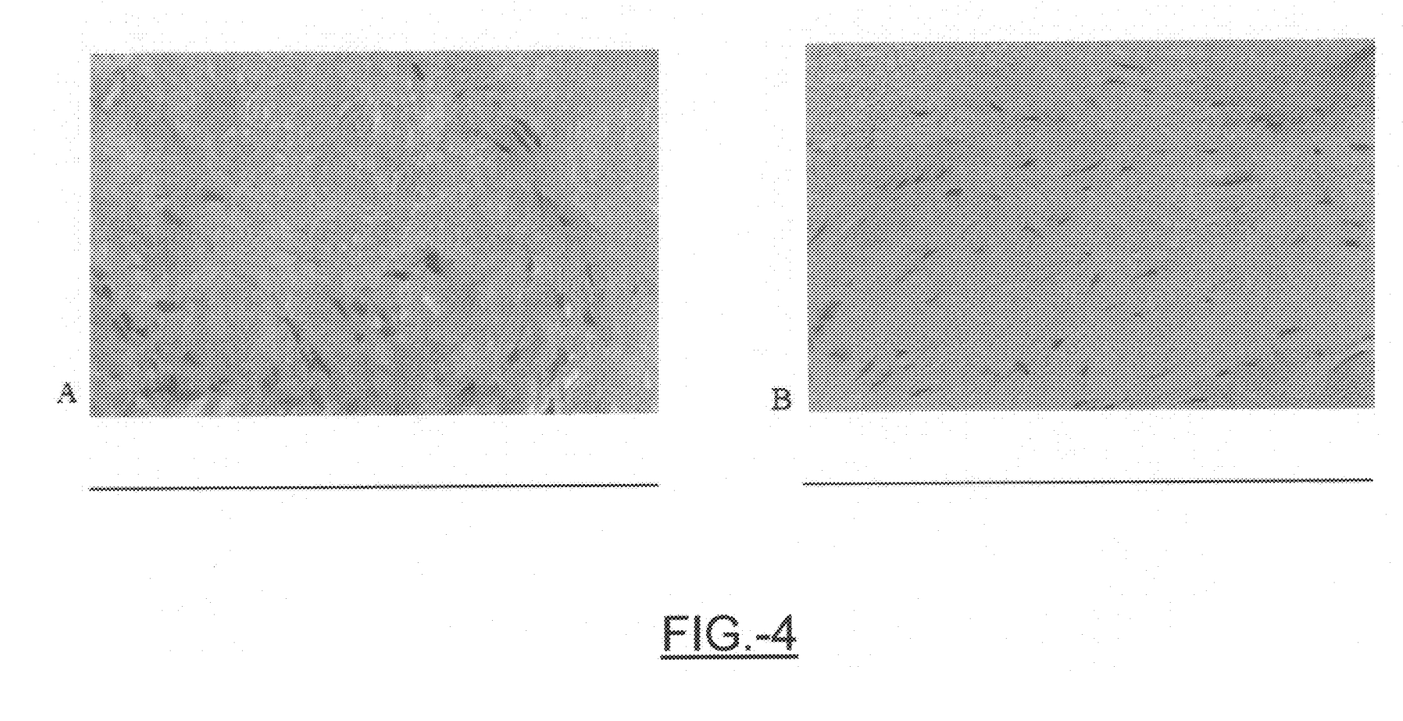
FIGS. 4A-4B are hematoxylin and eosin stains of bladder detrusor cells cultivated with urothelial induction and mechanical stimulation on day 18 on the membrane (FIGS. 4A and 4B show the movement of the cells within the membrane)
Figure 5:
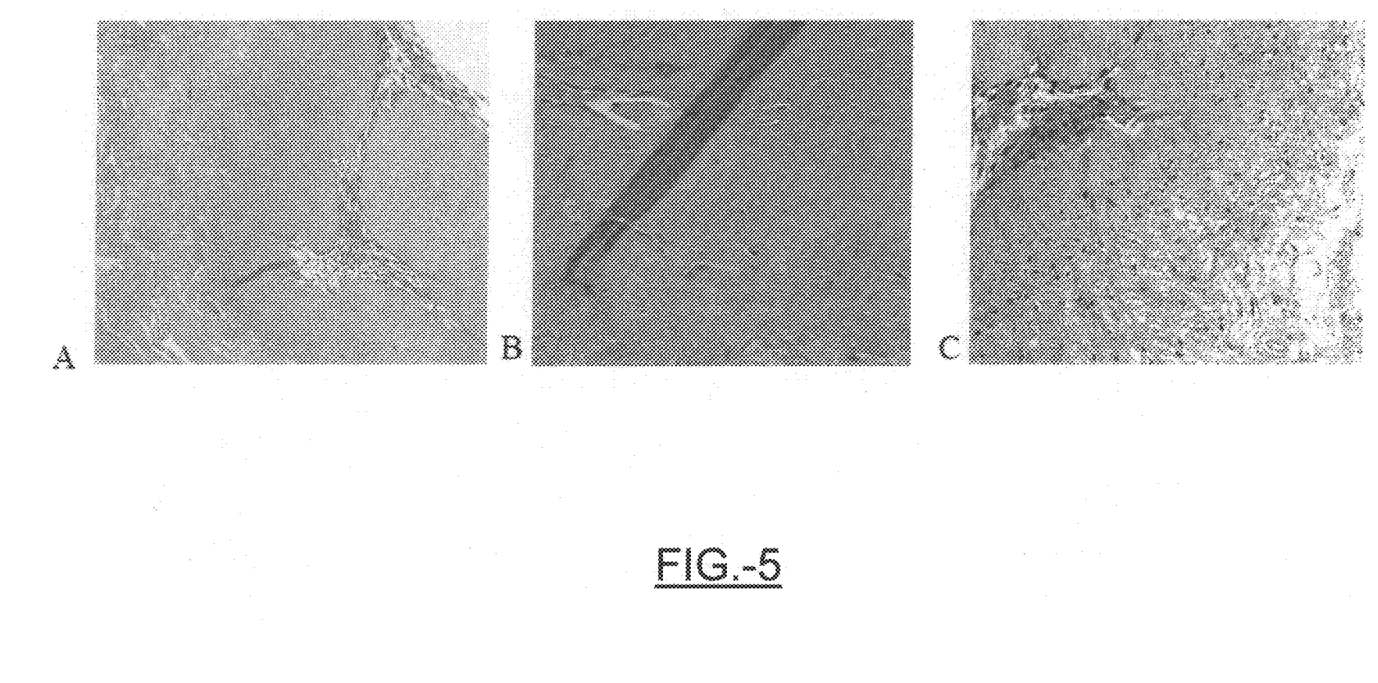
Figure 6:
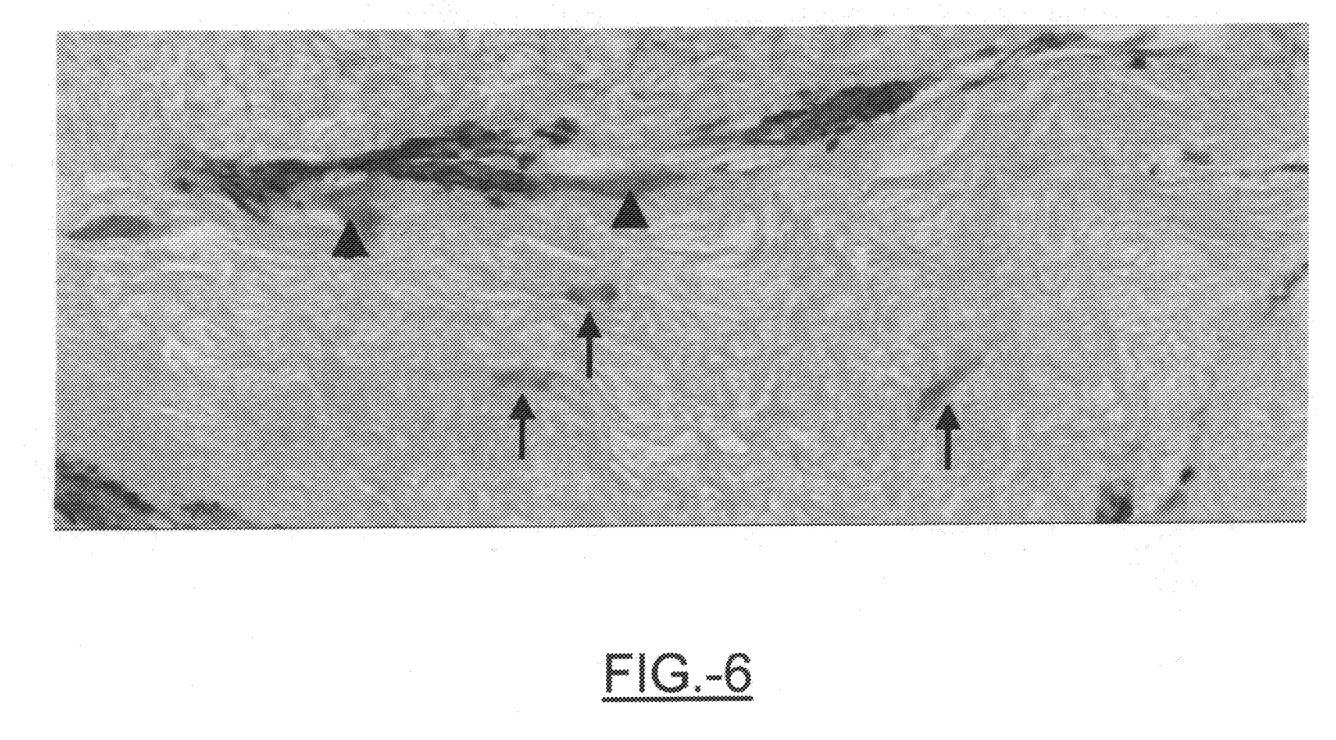
FIG. 6 is immunohistochemical SMA stains of the bladder detrusor cells cultivated with urothelial induction and mechanical stimulation on the membrane. Compared with SMC, the fibroblastic cells did not stain with alpha smooth muscle actin antibody and thus do not show the corresponding brown color.

The percentage of SMA-positive cells in the second group (i.e. cells cultivated with proliferative urothelial medium) was about 60% on day 32 (FIG. 4B) compared with 40% in the first group (i.e. cells cultivated with terminally differentiated urothelial medium) when the serum was depleted in three steps. Under the second conditions (medium conditioned with proliferating urothelium), the additional mechanical stretching not only induced cell penetration and migration in different directions in the presence of serum (day 1 to 28; FIG. 4, 5), but also increased the proportion of SMA-positive cells (FIG. 2C to 2F). In this culture system, more than 80% of the P3 cells stained positively for SMA on day 32 when the serum was reduced in three steps (FIG. 2C). The remaining 20% of the cell population (interstitial fibroblastic cells) stained positively for vimentin, whereas they showed negative staining for SMA and only weak sensitivity to the mechanical deformations and biochemical stimuli (FIG. 6). In cultures with a constant serum concentration (5% serum, day 1 to 32), the P3 cells migrated into the membrane under strain when they were fed with urothelium-conditioned medium, but showed SMA expression only in part (40% SMA-positive cells in medium conditioned with proliferating urothelium and 30% SMA-positive cells in medium conditioned with terminally differentiated urothelium).

FIGS. 4A and 4B show photographs of H & E stains of P3 cells on the acellular membrane in 20× magnification. The spatial movement of cells in the interior of the three-dimensional structure of the acellular membrane is evident with urothelial induction and mechanical stimulation on day 18 after application of the cells to the membrane (FIG. 4A, FIG. 4B). The cells loosen cell-cell adhesion during the migration. The degradation of the extracellular matrix by the migrating cells was detectable. The elongate shape of the migrating cells during stretching is particularly noteworthy.

FIGS. 5A to 5C show further photographs of H & E stains of the membrane-cell composites in 20× magnification. Penetration of the membrane by P3 tissue cells with urothelial induction and mechanical stimulation is evident. The highly mobile cells have moved over the entire area of the membrane and formed many layers thereon (FIG. 5A). They have penetrated far into the interior of the membrane in various directions and initially maintained cell-cell adhesion (FIG. 5A), with the extracellular matrix components being degraded, and have overcome their spatial barrier (FIG. 5A to 5C). The membrane was completely permeated by tissue cells after removal of serum on day 32 (FIG. 5C).

FIG. 6 shows a photograph of an SMA stain of a membrane-cell composite. The cells which have penetrated into the membrane are evident. The fibroblasts did not stain positively with SMA antibody with urothelial induction and mechanical stimulation. Compared with this, the smooth muscle cells showed a positive reaction with the antibody (brown color) under the same conditions. The interstitial fibroblastic cells are identified by arrows.

REFERENCES

1 Yoo J J, Meng J, Oberpenning F, Atala A. Bladder augmentation using allogenic bladder submucosa seeded with cells. *Urology*, 51: 221, 1998
2 Atala A. New methods of bladder augmentation. *BJU Int.*, 85 Suppl 3: 24, 2000
3 Zhang Y, Kropp B P, Lin H K, Cowan R, Cheng E Y. Bladder regeneration with cell-seeded small intestinal submucosa. *Tissue Eng*, 10: 181, 2004
4 Ram Liebig G, Meye A, Hakenberg O W. Haase M, Baretton G, Wirth M P. Induction of proliferation and differentiation of cultured urothelial cells on acellular biomaterials. *BJU Int*, 94:922, 2004
5 Lai J Y, Yoon C Y, Yoo J J, Wulf T, Atala A. Phenotypic and functional characterization of in vivo tissue engineered smooth muscle from normal and pathological bladders. *J Urol*, 168: 1853, 2002
6 Kropp B P, Zhang Y, Tomasek J J, Cowan R, Furness P D 3rd, Vaughan M B, Parizi M, Cheng E Y. Characterization of cultured bladder smooth muscle cells: assessment of in vitro contractility. *J Urol*, 162: 1779, 1999
7 Hashitani H, Yanai Y, Suzuki H. Role of interstitial cells and gap junctions in the transmission of spontaneous Ca2+ signals in detrusor smooth muscles of the guinea-pig urinary bladder. *J Physiol*, 559: 567, 2004
8 Drake M J, Hedlund P, Andersson K E, Brading A F, Hussain I, Fowler C. Morphology, phenotype and ultrastructure of fibroblastic cells from normal and neuropathic human detrusor: absence of myofibroblast characteristics. *J Urol*, 169: 1573, 2003
9 Bottger B A, Hedin U, Johansson S, Thyberg J. Integrin-type fibronectin receptors of rat arterial smooth muscle cells: isolation, partial characterization and role in cytoskeletal organization and control of differentiated properties. *Differentiation*, 41: 158, 1989
10 Hedin U, Bottger B A, Luthman J, Johansson S, Thyberg J. A substrate of the cellattachment sequence of fibronectin (Arg-Gly-Asp-Ser) is sufficient to promote transition of arterial smooth muscle cells from a contractile to a synthetic phenotype. *Dev Biol*, 133: 489, 1989
11 Hedin U, Bottger B A, Forsberg E, Johansson S, Thyberg J. Diverse effects of fibronectin and laminin on phenotypic properties of cultured arterial smooth muscle cells. *J Cell Biol*, 107:307, 1988
12 Baskin L S, Sutherland R S, Thomson A A, Hayward S W, Cunha G R. Growth factors and receptors in bladder development and obstruction. *Lab Invest*, 75: 157, 1996
13 Liu W, Li Y, Cunha S, Hayward G, Baskin L. Diffusable growth factors induce bladder smooth muscle differentiation. *In Vitro Cell Dev Biol Anim*, 36: 476, 2000
14 Camoretti-Mercado B, Liu H W, Halayko A J, Forsythe S M, Kyle J W, Li B. Physiological control of smooth muscle-specific gene expression through regulated nuclear translocation of serum response factor. *J Biol Chem*, 275: 30387, 2000
15 Stegemann J. P., Nerem R. M. Effect of mechanical stimulation on smooth muscle cell proliferation and phenotype. *BED*, Vol. 50, 2001 Bioengineering conference. ASME 2001
16 Galvin D J, Watson R W, Gillespie J I, Brady H, Fitzpatrick J M. Mechanical stretch regulates cell survival in human bladder smooth muscle cells in vitro. *Am J Physiol Renal Physiol*, 283: F1192, 2002
17 Albinsson S, Nordstrom I, Hellstrand P. Stretch of the vascular wall induces smooth muscle differentiation by promoting actin polymerization. *J Biol Chem*, 279: 34849, 2004
18 Zeidan A, Nordstrom I, Albinsson S, Malmqvist U, Sward K, Hellstrand P. Stretch-induced contractile differentiation of vascular smooth muscle: sensitivity to actin polymerization inhibitors. *Am J Physiol Cell Physiol*, 284: C1387, 2003
19 Upadhyay J, Aitken K J, Damdar C, Bolduc S, Bagli D J. Integrins expressed with bladder extracellular matrix after stretch injury in vivo mediate bladder smooth muscle cell growth in vitro. *J Urol*, 169: 750, 2003
20 Sjuve R, Haase H, Ekblad E, Malmqvist U, Morano I, Amer A. Increased expression of non muscle myosin heavy chain-B in connective tissue cells of hypertrophic rat urinary bladder. *Cell Tissue Res*, 304: 271, 2001

The invention claimed is:

1. A process for fabricating a urinary bladder tissue, comprising the steps of:
    providing a collagen based acellular tissue membrane obtained from one or more of urinary bladder, urinary bladder submucosa, aorta, urethra, small intestinal submucosa or dermal matrix, the acellular tissue membrane having a first side and an opposing second side;
    collecting smooth muscle cells and interstitial fibroblastic cells from a urinary bladder;
    collecting urothelial cells from a urinary bladder;
    culturing smooth muscle cells and interstitial fibroblastic cells in two dimensions between two to four passages to confluence;
    culturing the urothelial cells in two dimensions to confluence in a plurality of passages;
    seeding the first side of the acellular tissue membrane with smooth muscle cells and interstitial fibroblastic cells from a selected passage;
    seeding the second side of the acellular tissue membrane with urothelial cells from a selected passage; and
    culturing the seeded acellular tissue membrane by simultaneous mechanical and biochemical stimulation; wherein
    the mechanical stimulation comprises applying tension cyclically to the seeded acellular tissue membrane, wherein the periodicity of the tension comprises a stretching period of about 10 seconds to about 20 seconds and a relaxing period of about 10 seconds, and the strain resulting therefrom is approximately 10%, and the mechanical stimulation continues until the acellular tissue membrane comprises confluently cultured cells; and the biochemical stimulation includes culturing the seeded acellular tissue membrane in a serum-conditioned culture medium, wherein the serum-conditioned culture medium comprises autologous serum or fetal bovine serum conditioned by proliferating urothelial cells, and wherein the serum-conditioned culture medium comprises about 5% serum for a first cultivation period, 1% serum for a second cultivation period, and about 0% serum for a third cultivation period; and resulting in a urinary bladder tissue comprising:

at least one layer of smooth muscle cells and interstitial fibroblastic cells, wherein said layer comprises between 75% and 85% smooth muscle cells and between 15% and 25% fibroblastic cells; and at least one layer of urothelial cells bounded by the acellular tissue membrane.

2. The process of claim 1, wherein the first cultivation period is about 14 days, the second cultivation period is about 13 days, and the third cultivation period is about three days.

3. A fabricated urinary bladder tissue made by the process of claim 2.

* * * * *